(12) United States Patent
Fang et al.

(10) Patent No.: US 8,794,830 B2
(45) Date of Patent: Aug. 5, 2014

(54) CATHETER WITH DIGITIZED TEMPERATURE MEASUREMENT IN CONTROL HANDLE

(75) Inventors: Itzhak Fang, Irvine, CA (US); Thomas Selkee, Claremont, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 85 days.

(21) Appl. No.: 12/904,050

(22) Filed: Oct. 13, 2010

(65) Prior Publication Data

US 2012/0095362 A1   Apr. 19, 2012

(51) Int. Cl.

| | |
|---|---|
| *G01K 7/00* | (2006.01) |
| *A61B 5/00* | (2006.01) |
| *A61B 5/01* | (2006.01) |
| *A61M 39/02* | (2006.01) |
| *G01K 5/22* | (2006.01) |
| *G01K 13/00* | (2006.01) |
| *A61B 10/00* | (2006.01) |
| *A61B 17/00* | (2006.01) |
| *A61B 18/00* | (2006.01) |

(52) U.S. Cl.
CPC ........... *A61B 5/01* (2013.01); *A61B 2010/0019* (2013.01); *A61B 2017/00084* (2013.01); *A61B 2017/00092* (2013.01); *A61B 2018/00791* (2013.01); *A61B 2018/00821* (2013.01); *A61B 2562/0271* (2013.01); *A61M 39/0247* (2013.01); *G01K 5/22* (2013.01); *G01K 13/00* (2013.01); *G01K 13/002* (2013.01)
USPC .......................................... 374/181; 600/549

(58) Field of Classification Search
USPC .......... 600/301, 345, 361, 549; 374/181, 182, 374/164, E15.001, E7.004, E7.013, E1.002, 374/E7.016; 376/247; 606/34, 41; 340/518, 340/525, 691.6, 815.53; 607/105, 113, 99; 136/222; D10/103; 703/5; 439/629; 345/156
See application file for complete search history.

(56) References Cited

U.S. PATENT DOCUMENTS

| | | | |
|---|---|---|---|
| 3,810,138 A * | 5/1974 | Thompson et al. ............ 340/518 |
| 4,673,300 A * | 6/1987 | Wilhelmson et al. ......... 374/182 |
| 4,718,777 A * | 1/1988 | Mydynski et al. ............. 374/181 |
| RE34,507 E | 1/1994 | Egawa et al. |
| 5,425,375 A | 6/1995 | Chin et al. |

(Continued)

OTHER PUBLICATIONS

MAXIM/Dallas Semiconductor, Implementing Cold-Junction Compensation in Thermocouple Applications, Mar. 19, 2007, pp. 1-8.*

(Continued)

*Primary Examiner* — Brian Szmal
(74) *Attorney, Agent, or Firm* — Christie, Parker & Hale, LLP (57) ABSTRACT

A temperature sensing catheter with improved accuracy is provided. The catheter includes a catheter shaft having a proximal end and a distal end, and a first pair of conductors extending through the catheter shaft. Each one of the first pair of conductors has a first end and a second end, and the first ends of the first pair of conductors are coupled to each other at the distal end of the catheter shaft to form a first thermocouple. A handle is coupled to the proximal end of the catheter shaft and receives the second ends of the first pair of conductors, and the handle includes a digitizing circuit coupled to the second ends of the first pair of conductors for digitizing a voltage signal of the first thermocouple.

20 Claims, 12 Drawing Sheets

(56) References Cited

U.S. PATENT DOCUMENTS

| | | | |
|---|---|---|---|
| 5,871,481 A * | 2/1999 | Kannenberg et al. | 606/34 |
| 5,893,885 A | 4/1999 | Webster, Jr. | |
| 5,897,529 A | 4/1999 | Ponzi | |
| 5,964,757 A | 10/1999 | Ponzi | |
| 6,064,905 A | 5/2000 | Webster, Jr. et al. | |
| 6,066,125 A | 5/2000 | Webster, Jr. | |
| 6,477,396 B1 | 11/2002 | Mest et al. | |
| 6,939,350 B2 | 9/2005 | Phan | |
| 6,942,382 B2 | 9/2005 | Demeocq | |
| 7,252,664 B2 | 8/2007 | Nasab et al. | |
| 7,366,557 B2 | 4/2008 | Bautista | |
| 7,377,906 B2 | 5/2008 | Selkee | |
| 2006/0089637 A1 | 4/2006 | Werneth et al. | |
| 2006/0106375 A1 | 5/2006 | Werneth et al. | |
| 2008/0161788 A1 | 7/2008 | Dando et al. | |
| 2009/0118604 A1 * | 5/2009 | Phan et al. | 600/345 |
| 2010/0036213 A1 * | 2/2010 | Rieth | 600/301 |

OTHER PUBLICATIONS

Williams, *Thermocouple Measurement*, Linear Technology (Application Note 28), 1988, 20 Sheets.

Anderson et al., *Thermocouple Measurements with ΔΣ ADCs*, Texas Instrutments (Application Report SBAA134), 2005, 17 Sheets.

Julicher, *Simplified Thermocouple Interfaces and PICmicro® MCUs*, Microchip (Application Note 844), 2002, 12 Sheets.

Lepkowski, *Temperature Measurement Circuits for Embedded Applications*, Microchip (Application Note 929), 2004, 22 sheets.

Analog Devices, Inc., "AD8494: Precision Thermocouple Amplifiers with Cold Junction Compensation—Revision 0", Product Data Sheet, Jul. 31, 2010, pages 1-16, XP002668475.

Extended European Search Report dated Feb. 21, 2012, in corresponding Application No. 11184777.8 (9 pages).

* cited by examiner

CATHETER WITH DIGITIZED TEMPERATURE MEASUREMENT IN CONTROL HANDLE

BACKGROUND

1. Field

Aspects of embodiments of the present invention relate to catheters and, in particular, to a catheter with improved temperature measurement capability.

2. Description of Related Art

Catheters have been in common use in medical practice for many years. Applications of catheters include stimulating and mapping electrical activity in the heart and ablating sites of aberrant electrical activity. Such catheters are also referred to as electrode catheters. In use, an electrode catheter is inserted into a major vein or artery, e.g., femoral artery, and then guided into the location of interest within the body, e.g., the chamber of the heart where aberrant electrical activity within the heart is located.

Once the catheter reaches the intended location inside the patient's body, the physician uses an ablation procedure to destroy the tissue causing the aberrant electrical activity in an attempt to remove the electrical signal irregularities and restore normal heart beat or at least an improved heart beat. A typical ablation procedure involves providing a reference electrode, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, a thin transparent coating of dehydrated blood protein can form on the surface of the electrode. If the temperature continues to rise, this dehydrated layer can become progressively thicker, resulting in char and/or thrombus on the electrode surface. The creation of char and thrombus is unsafe, as the char and thrombus can be dislodged from the electrode during the procedure or during removal of the catheter after the procedure.

In clinical practice, it is desirable to reduce or eliminate the formation of char and thrombus and, for certain cardiac arrhythmias, to create larger and/or deeper lesions. One method for accomplishing this end is to monitor the temperature of the ablation electrode and to control the RF current delivered to the ablation electrode based on this temperature. If the temperature rises above a pre-selected value, the current is reduced until the temperature drops below this value. Therefore, the tip of the catheter, e.g., a tip ablation electrode, is equipped for temperature measurement. Among the many temperature transducers available for temperature measurement, thermocouple (TC) is commonly used for its simple construction and ruggedness.

Using TC as temperature sensor requires the use of special cables and connectors made of the same materials as the TC wires, otherwise, material transition in the signal path (e.g., connectors) forms additional junctions of dissimilar metal and additional thermal junctions. However, there are no known off-the-shelf connectors for disposable medical device (e.g., catheter) that are implemented with TC materials such as constantan pins and sockets, and such pins and sockets make a challenging design in conjunction with other medical device connector requirements such as high mating cycles requirement, and high pin density and quality of connection. Therefore, the common disposable medical device is typically connected through off-the-shelf connectors that do not use the appropriate TC material. As such, any material differences between the two sides of the connector translate to measurement error.

Accordingly, it is desirable to provide an improved catheter equipped with TC for temperature measurement. In particular, it is desirable to reduce the measurement errors of TC caused by additional junctions of dissimilar metals and additional thermal junctions.

SUMMARY

Exemplary embodiments of the present inventions provide a catheter with improved TC temperature measurement capability. According to the exemplary embodiments, the catheter includes a TC signal processing circuit at the handle of the catheter to digitize TC voltage signal such that TC connections and wirings within the handle may be reduced, and digital values of the TC voltage signal may be transmitted from the handle to a host via a digital link without using TC wires.

According to an embodiment of the present invention, a catheter includes a catheter shaft having a proximal end and a distal end. The catheter shaft typically includes a proximal catheter body, an intermediate deflectable portion, and a distal tip section that includes a tip ablation electrode where temperature sensing is desirable. A first pair of conductors extend through the catheter shaft, and each one of the first pair of conductors has a first end and a second end. The first ends of the first pair of conductors are coupled to each other at the distal end of the catheter shaft to form a first thermocouple. A handle is coupled to the proximal end of the catheter shaft and receives the second ends of the first pair of conductors. The handle includes a digitizing circuit therein coupled to the second ends of the first pair of conductors for digitizing a voltage signal of the first thermocouple.

The digitizing circuit may include an isothermal block thermally coupled to the second ends of the first pair of conductors. The digitizing circuit may include a temperature sensor for sensing a temperature of the isothermal block. The digitizing circuit may include a low pass filter for filtering the voltage signal of the first thermocouple. The digitizing circuit may include an amplifier for amplifying the voltage signal of the first thermocouple. The digitizing circuit may include an analog-to-digital converter for generating a digital value corresponding to the voltage signal of the first thermocouple. The digitizing circuit may be adapted to calculate a temperature value of the first thermocouple based on the digital value. The digitizing circuit may be adapted to perform cold-junction compensation. The digitizing circuit may be capable of being identified by at least one digital address. The catheter may further include a second pair of conductors extending through the catheter shaft. Each one of the second pair of conductors has a first end and a second end, and the first ends of the second pair of conductors are coupled to each other at a portion between the proximal end and distal end of the catheter shaft to form a second thermocouple. The handle receives the second ends of the second pair of conductors. The digitizing circuit is coupled to the second ends of the second pair of conductors, and is adapted to digitize a voltage signal of the second thermocouple.

The digitizing circuit may be adapted to calculate a temperature value of the second thermocouple based on the digitized voltage signal of the second thermocouple. The digitizing circuit may be capable of being identified by at least two digital addresses including a first digital address corresponding to the first thermocouple and a second digital address corresponding to the second thermocouple. The digitizing circuit may include a digital interface for transmitting data corresponding to the voltage signal of the first thermocouple.

According to an embodiment of the present invention, a system for measuring temperature is provided. The system includes a host and a catheter in data communication with the host. The catheter includes a catheter shaft having a proximal end and a distal end, and a pair of conductors extending through the catheter shaft. Each one of the pair of conductors has a distal end and a proximal end. The distal ends of the pair of conductors are coupled to each other at the distal end of the catheter shaft to form a thermocouple. A handle is coupled to the proximal end of the catheter shaft and receives the proximal ends of the pair of conductors. The handle includes a digitizing circuit therein coupled to the proximal ends of the pair of conductors for digitizing a voltage signal of the thermocouple.

According to an embodiment of the present invention, a method of measuring temperature with a catheter is provided. The method includes sensing a temperature at a distal end of a catheter shaft of the catheter by a thermocouple, transmitting a voltage signal of the thermocouple to a handle coupled to a proximal end of the catheter shaft, and digitizing the voltage signal of the thermocouple by a circuit located at the handle to generate a digital value corresponding to the temperature.

The method may further include performing cold-junction compensation by the circuit located at the handle. The method may further include processing the voltage signal of the thermocouple by a low pass filter. The method may further include transmitting the digital value to a host located away from the handle by a digital link.

BRIEF DESCRIPTION OF THE DRAWINGS

The features and aspects of the present invention will be more apparent from the following detailed description in conjunction with the accompanying drawings, in which.

DETAILED DESCRIPTION

Embodiments of the present invention will be described more fully hereinafter, in which exemplary embodiments are shown. This disclosure may, however, be embodied in many different forms and is not be construed as limited to the exemplary embodiments set forth herein. Here, when a first element is described as being coupled or connected to a second element, the first element may be directly connected to the second element or indirectly connected to the second element via one or more third elements.

Conventional catheter receives a TC (thermocouple) voltage signal from a catheter shaft and passes the TC voltage signal via a plurality of conductors through a handle of the catheter to a remote host or controller for further processing of the TC voltage signal to determine the temperature sensed by the TC. Such temperature interface system suffers from signal degradation due to one or more connections of dissimilar TC wires used at connector interfaces. The connectors also introduce variable pin connection resistance that produces a voltage drop between connections, thus causing degradation in TC signal resolution.

Aspects of the present invention are related to an improved catheter equipped with TC for temperature sensing. Exemplary embodiments of the present invention disclose a catheter equipped with a TC signal-processing circuit at the control handle of the catheter such that the TC voltage signal may be processed (e.g., digitized) by the TC signal-processing circuit in the handle and outputted as digital data to a host via a digital data link.

Figure 1:
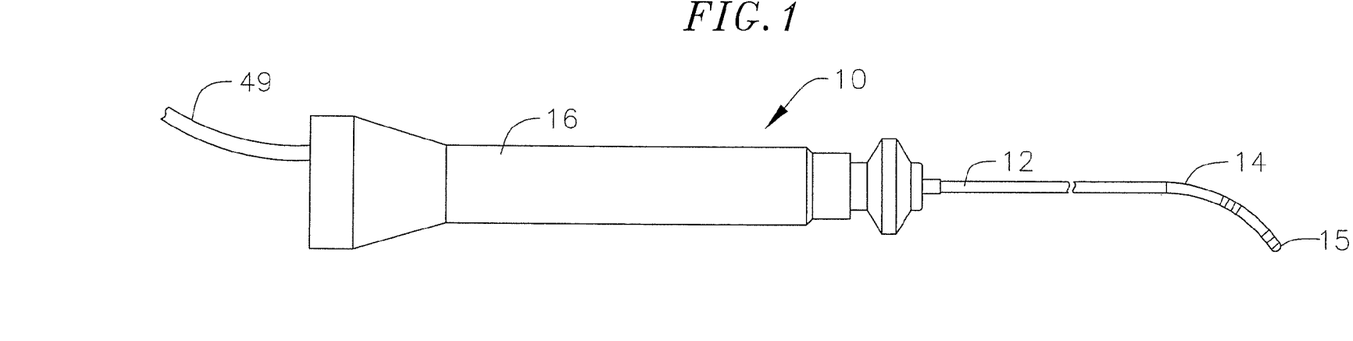
FIG. 1 is a side view of a catheter according to an embodiment of the present invention.

FIG. 1 is a drawing illustrating a side view of a catheter 10 according to an embodiment of the present invention. The catheter 10 includes an elongated catheter shaft or body 12 having proximal and distal ends, an intermediate section 14 with uni- or bi-directional deflection distal of the catheter shaft 12, a tip section 15 with a tip electrode 17 at a distal end of the intermediate section, and a handle 16 (e.g., a control handle) at the proximal end of the catheter shaft 12.

Figure 2A:
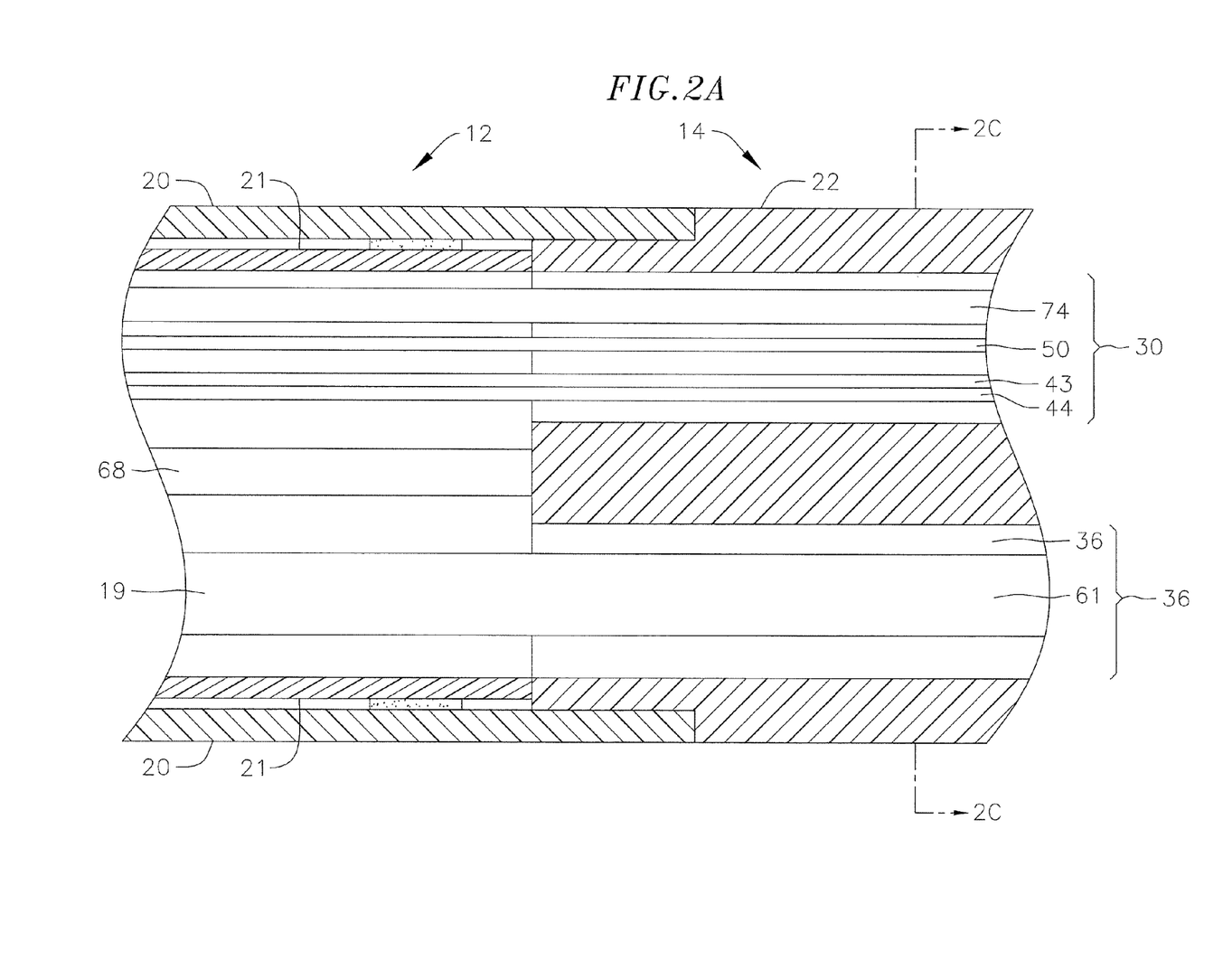
FIG. 2A is a side cross-sectional view of the catheter of FIG. 1, including a junction of a catheter body and an intermediate section, along a first diameter.
Figure 2B:
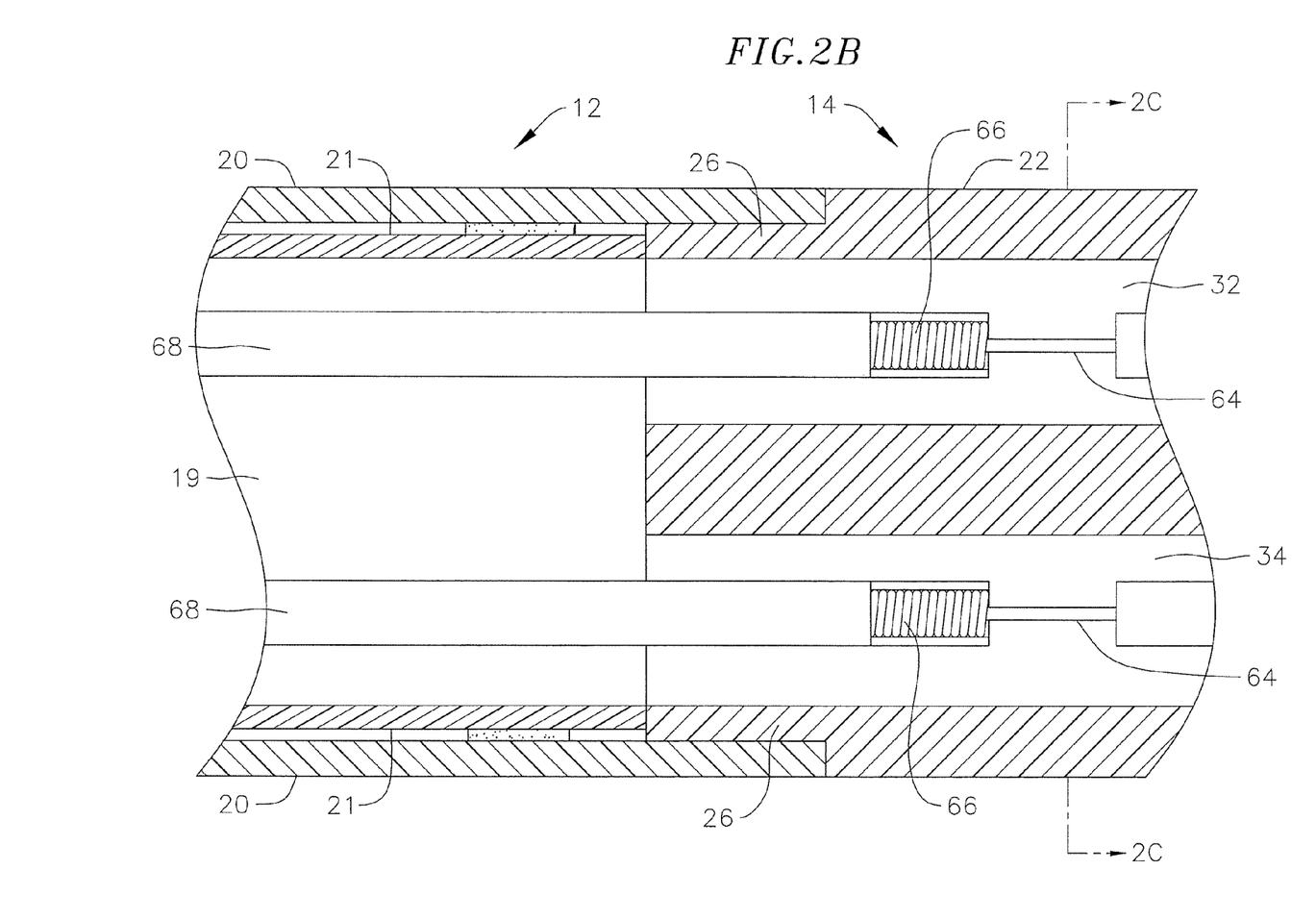
FIG. 2B is a side cross-sectional view of the catheter of FIG. 1, including a junction of a catheter body and an intermediate section, along a second diameter generally perpendicular to the first diameter.

As shown in FIGS. 2A and 2B, the catheter body 12 comprises an elongated tubular construction having a single, axial or central lumen 19. The catheter body 12 is flexible, i.e., bendable, but substantially non-compressible along its length. The catheter body 12 can be of any suitable construction and made of any suitable material. A presently preferred construction comprises an outer wall 20 made of polyurethane or PEBAX. The outer wall 20 comprises an embedded braided mesh of stainless steel or the like to increase torsional stiffness of the catheter body 12 so that, when the control handle 16 is rotated, the intermediate section 14 of the catheter 10 is able to rotate in a corresponding manner.

The outer diameter of the catheter body 12 is not critical, but is preferably no more than about 9 french, more preferably about 7 french. Likewise, the thickness of the outer wall 20 is not critical, but is thin enough so that the central lumen 19 can accommodate puller wires, one or more lead wires, and any other desired wires, cables or tubes. If desired, the inner surface of the outer wall 20 is lined with a stiffening tube 21 to provide improved torsional stability. In one embodiment, catheter 10 has an outer wall 20 with an outer diameter of from about 0.090 inches to about 0.094 inches and an inner diameter of from about 0.061 inches to about 0.065 inches.

Figure 2C:
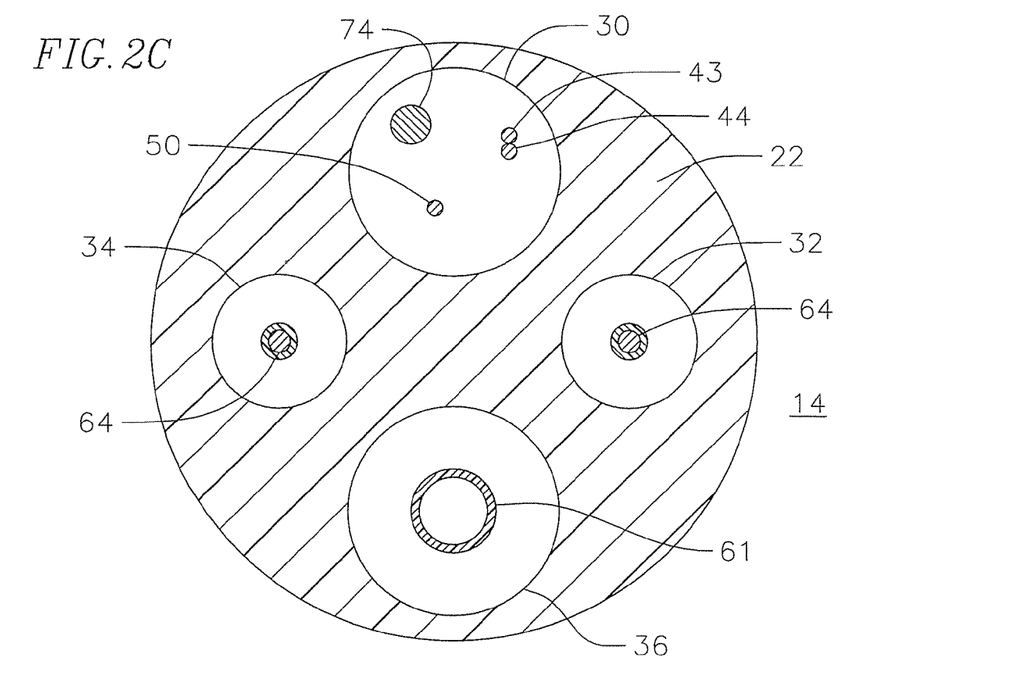
FIG. 2C is an end cross-sectional view of the catheter of FIGS. 2A and 2B, taken along line C-C.
Figure 2D:
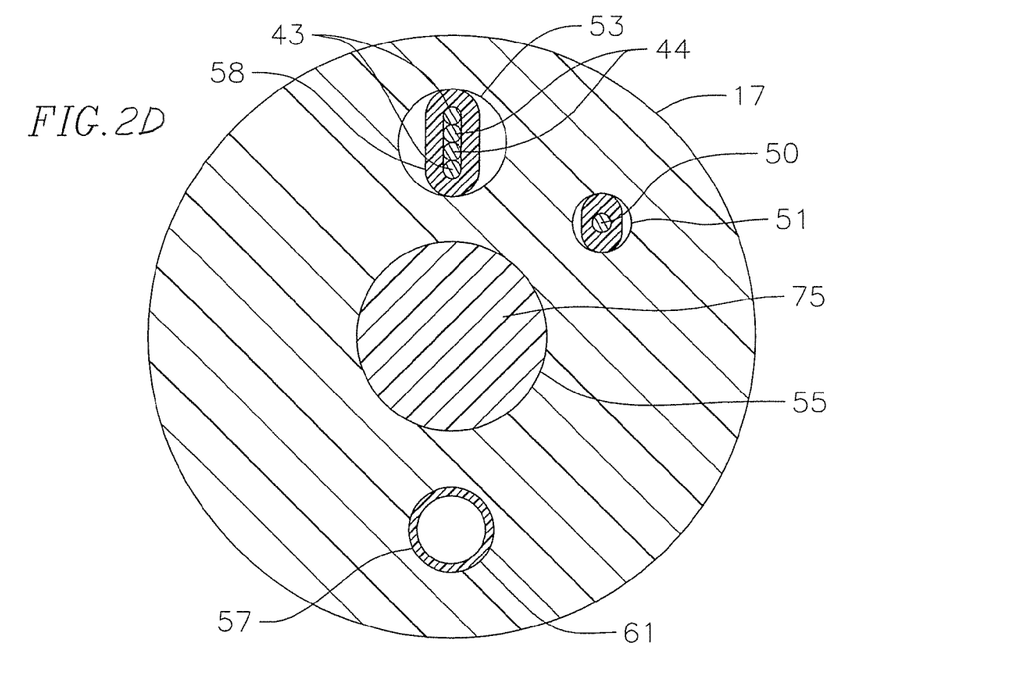
FIG. 2D is an end cross-sectional view of the catheter of FIG. 4, taken along line 2D-2D.
Figure 3:
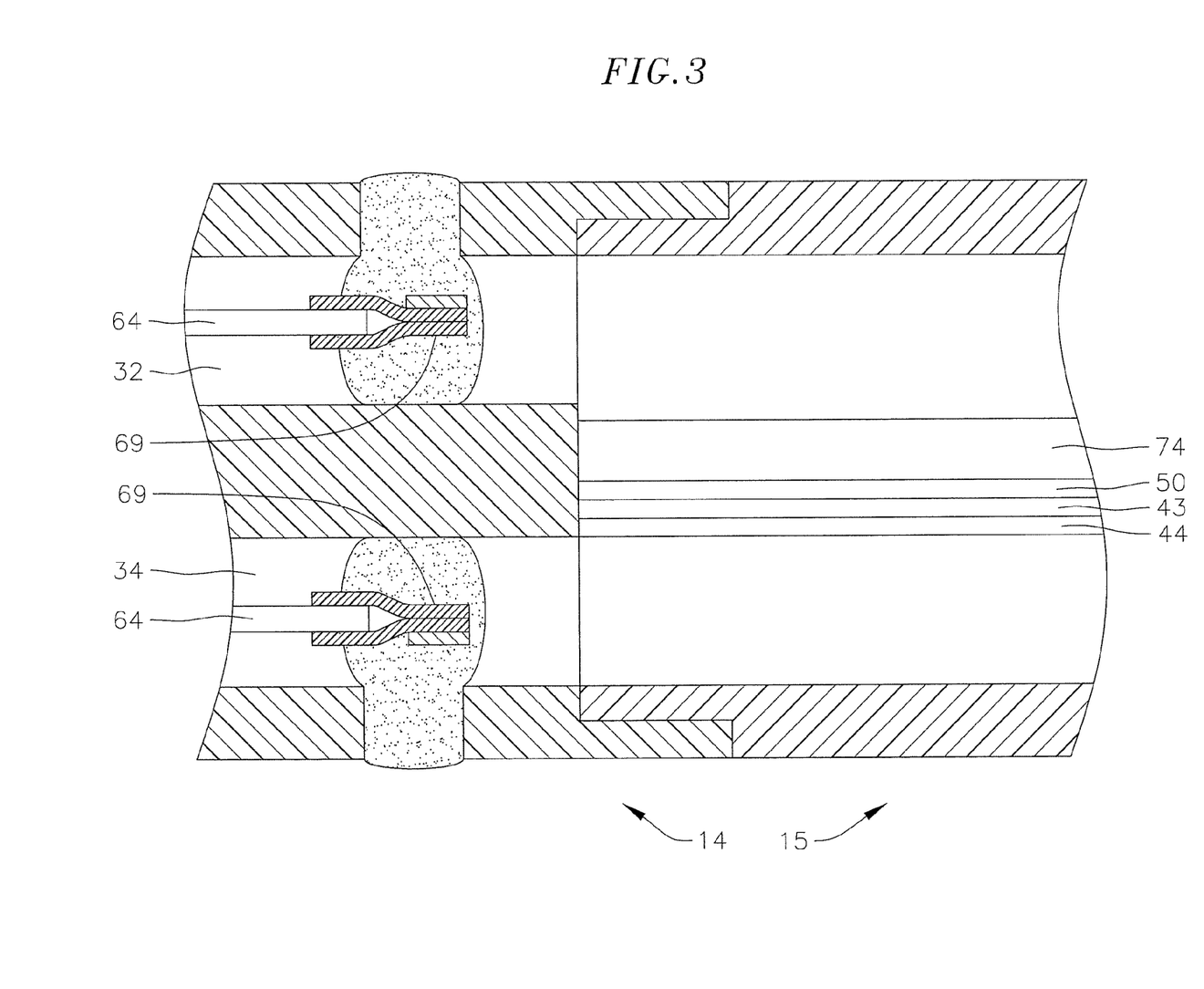
FIG. 3 is a side cross-sectional view of the catheter of FIG. 1, including a junction between an intermediate section and a connector tubing.

The intermediate section 14 comprises a short section of tubing 22 having multiple lumens, as also shown in FIG. 2C. In one embodiment, a first lumen 30 carries one or more lead wires 50, thermocouple TC (e.g., thermocouple wires 43 and 44) for monitoring tissue temperature in the tip electrode 17, and a cable 74 for an electromagnetic position 75 sensor housed in the tip section 14. Each of second and third lumens 32, 34 carries a puller wire 64. A fourth lumen 35 carries an irrigation tube 61 for supplying fluid to the tip electrode. The tubing 22 is made of a suitable non-toxic material that is preferably more flexible than the catheter body 12. In one embodiment, the tubing 22 is braided polyurethane, i.e., polyurethane with an embedded mesh of braided stainless steel or the like. The number of lumens or the size of each lumen is not critical, but is sufficient to house the lead wires, puller wire(s), electromagnetic sensor cable, thermal sensors and/or irrigation tube(s) depending on the embodiment.

A preferred means for attaching the catheter body 12 to the intermediate section 14 is illustrated in FIGS. 2a and 2b. The proximal end of the intermediate section 14 comprises an outer circumferential notch 26 that receives the inner surface of the outer wall 20 of the catheter body 12. The intermediate section 14 and catheter body 12 are attached by glue or the like.

If desired, a spacer (not shown) can be located within the catheter body between the distal end of the stiffening tube 21 and the proximal end of the intermediate section. The spacer provides a transition in flexibility at the junction of the catheter body and intermediate section, which allows the junction to bend smoothly without folding or kinking. A catheter having such a spacer is described in U.S. Pat. No. 5,964,757, the entire disclosure of which is incorporated herein by reference.

Figure 4:
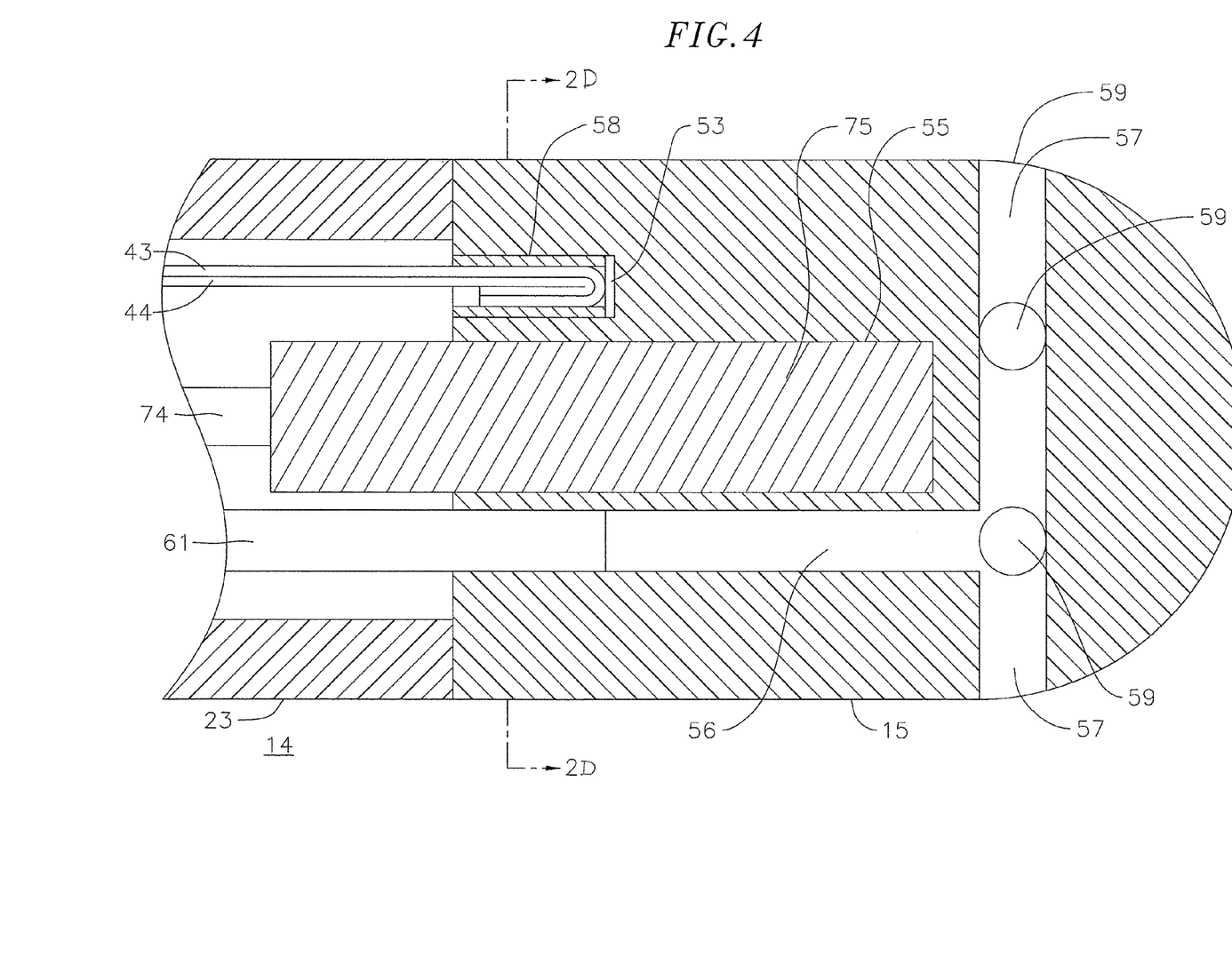
FIG. 4 is a side cross-sectional view of the catheter of FIG. 1, including a junction between a connector tubing and a tip electrode.

As illustrated in FIG. 4, the tip section 15 includes the tip electrode 17 which may be connected to the tubing 22 of the intermediate section 14 by means of a single lumen connector tubing 23. The connector tubing provides space for the electromagnetic position sensor 75 and the various components extending from the tubing 22 to reorient themselves as needed for anchoring in the tip electrode 17. To that end, a distal surface of the tip electrode is provided with blind holes. In the disclosed embodiment, blind hole 51 is provided to receive a distal end of the lead wire 50, blind hole 53 to receive a distal end of the TC, and blind hole 55 to receive a distal end of the electromagnetic sensor 75. Irrigation passage 56 is also formed in the tip electrode to receive a distal end of the irrigation tubing 61. The passage 55 is in communication with transverse branches 57 and fluid ports 59 allowing fluid delivered through the tubing 61 to pass to outside of the tip electrode.

As shown in FIG. 2B, the puller wires 64 are provided for bi-directional deflection of the intermediate section 14. The puller wires 64 extend through the catheter body 12, are anchored at their proximal ends to the control handle 16, and at their distal ends to the tubing 23 near the distal end of the intermediate section 14 by means of a T-bar anchor, as generally described in U.S. Pat. Nos. 5,893,885 and 6,066,125, the entire disclosures of which are incorporated herein by reference. The puller wires are made of any suitable metal, such as stainless steel or Nitinol, and are preferably coated with Teflon® or the like. The coating imparts lubricity to the puller wire 64. The puller wire 64 preferably has a diameter ranging from about 0.006 to about 0.010 inch.

A compression coil 66 is situated within the catheter body 12 in surrounding relation to each puller wire 64, as shown in FIG. 2B. The compression coil 66s extend from the proximal end of the catheter body 12 to the proximal end of the intermediate section 14. The compression coils 66 are made of any suitable metal, preferably stainless steel. Each compression coil 66 is tightly wound on itself to provide flexibility, i.e., bending, but to resist compression. The inner diameter of the compression coil 66 is preferably slightly larger than the diameter of the puller wire 64. The Teflon® coating on the puller wire 64 allows it to slide freely within the compression coil 66. The outer surface of each compression coil 66 is covered by a flexible, non-conductive sheath 68, e.g., made of polyimide tubing.

Examples of suitable catheter shaft construction are described and depicted in U.S. Pat. Nos. 6,064,905, 6,477,396 and 7,366,557, the entire disclosure of these patents are incorporated herein by reference.

Longitudinal movement of the puller wires 64 relative to the catheter body 12, which results in deflection of the intermediate section 14, is accomplished by suitable manipulation of the control handle 16. Examples of suitable control handles for use in the present invention are disclosed in U.S. Pat. Nos. Re 34,502, 5,897,529, and 7,377,906, the entire disclosures of which are incorporated herein by reference.

Figure 5:
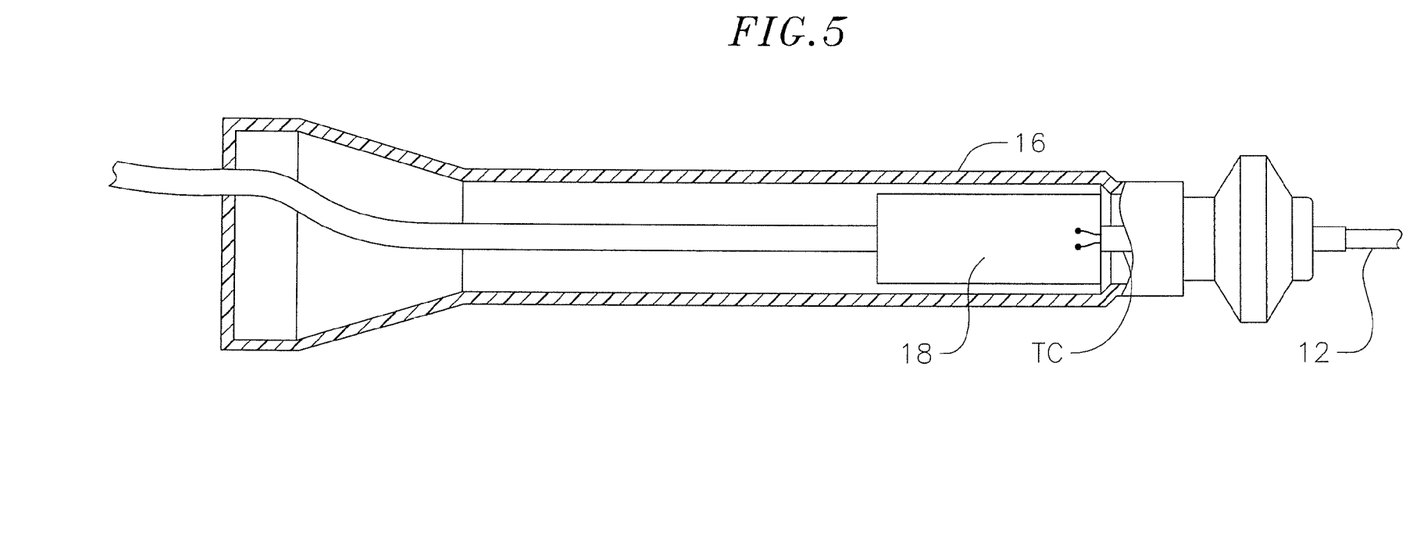
FIG. 5 is a side cross-sectional view of a control handle of the catheter in FIG. 1.

FIG. 5 is a drawing illustrating a side cross-sectional view of the handle 16 of the catheter 10. FIG. 5 conceptually shows that a circuit board 18 is located in the handle 16 and is connected to the TC extending from the catheter shaft 12. Here, the handle 16 and circuit board 18 may have any suitable shapes and sizes. As one of ordinary skill in the art, the location of the circuit board within the handle can vary depending on the structures and components within the handle, such as mechanisms for controlling deflection of the intermediate section 14 and various wires, cables and tubings that extend through the control handle and distally along the catheter shaft and beyond. The circuit board 18 includes a TC signal processing circuit that interfaces with the TC 20 such that the voltage signal from the TC 20 may be processed, digitized, and outputted to a host.

The TC, for example, is formed by an enameled wire pair where one wire is the copper wire 43, e.g., a number 40 copper wire and the other wire 44 is a constantan wire. The wires 43 and 44 are electrically isolated from each other except at their distal ends where they are connected together (e.g., twisted together), covered with a short piece of plastic tubing 58, e.g., polyamide, and covered with epoxy. The plastic tubing 58 is then attached in a distal section of blind hole 53 in the tip electrode 17, by polyurethane glue or the like.

The wires 43 and 44 extend through the central lumen 19 of the catheter shaft 12 and are connected to the circuit board 18 in the handle 16. The wires 43 and 44 are constructed of different metals or metal alloys and are connected together at the sensing end (i.e., the tip electrode 17 of the catheter shaft), which is referred as the hot-junction. The TC outputs a voltage difference (TC voltage signal) across the other ends of the wires 43 and 44 connected to the circuit board 18, referred to as the cold-junction, which is maintained at a known temperature. The cold-junction may be warmer than the hot-junction in some applications. In that case, the polarity of the TC's output voltage simply reverses. Thus, the TC measures the temperature difference between its hot and cold junctions, rather than absolute temperature at the cold-junction. Output voltages of various TCs have been tabulated for commonly used pairs of metals and alloys. The standard pairs are designated by single capital letters, such as "T" for constantan-copper TC, which is the most commonly used TC type for medical applications, due to its relatively high accuracy and appropriate linear range. The tabulated data is based on an assumed cold-junction temperature of 0° C. Therefore, to obtain the absolute temperature of the hot-junction sensing point, one must measure the cold-junction temperature and adjust the TC's output voltage accordingly. This technique is called cold-junction compensation.

Figure 6:
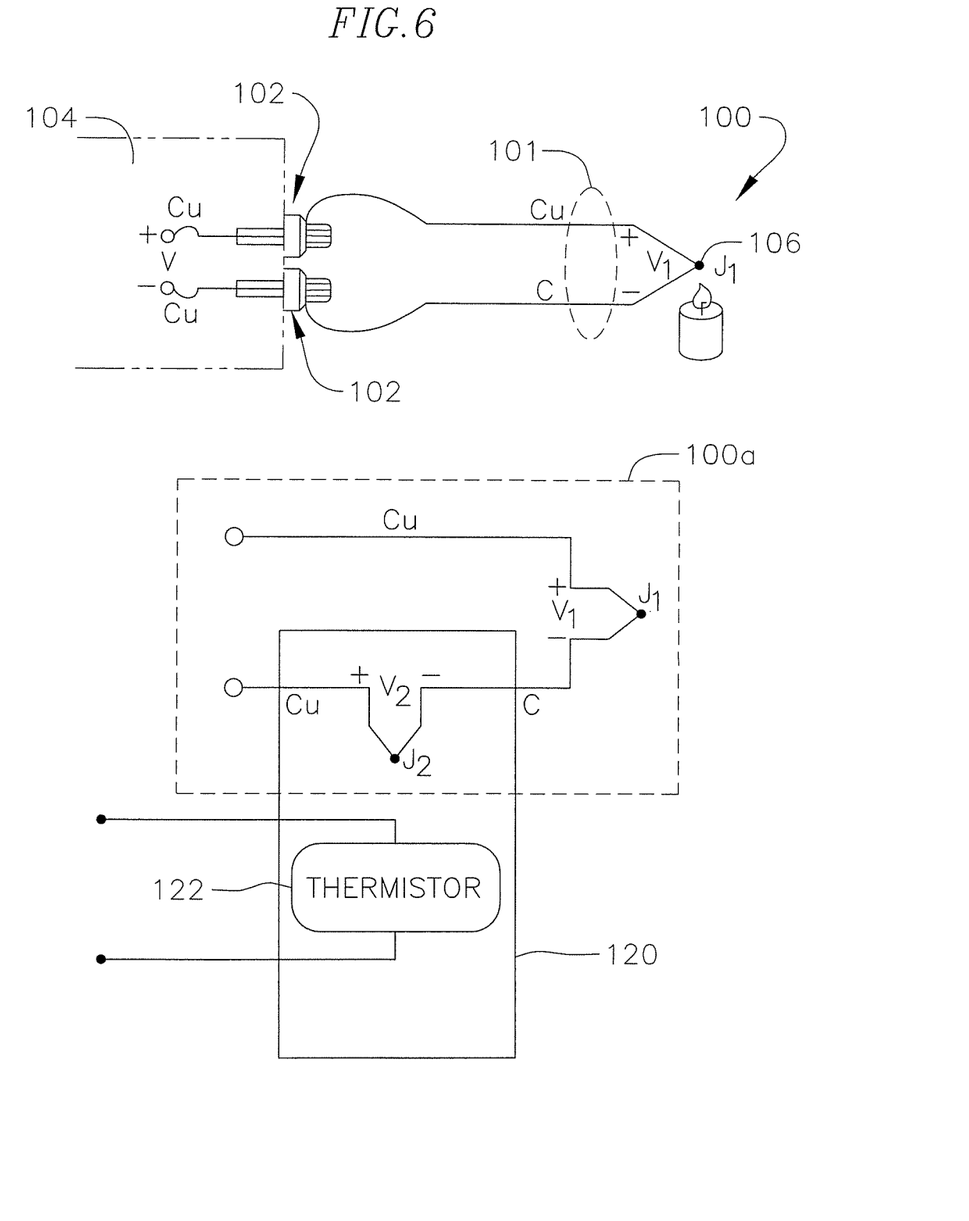
FIG. 6 is a drawing illustrating a TC measurement circuit and its equivalent circuit schematic.

FIG. 6 is a drawing illustrating a TC measurement circuit 100 and its equivalent circuit schematic.

Referring to FIG. 6, the TC measurement circuit 100 includes a T-type TC 101 that is connected to connectors 102 of an instrument 104. A hot-junction 106 is placed near an object to sense its temperature. The TC measurement circuit 100 is schematically represented by its equivalent circuit 100a, in which $J_1$ represents the hot-junction 106, and $J_2$ represents the cold-junction (i.e., connections between the TC 101 and the connectors 102). The cold-junction $J_2$ is on an isothermal block 120 (or isothermal barrier) so that the absolute temperature of the cold-junction $J_2$ can be determined.

The temperature of the isothermal block 120 may be measured by, for example, a suitable thermistor 122 such that a reference temperature may be determined. An amplifier with sufficient gain may be provided to amplify the TC voltage signal to cover the desired temperature range of the TC. Since the TC 101 is inherently a non-linear device, the TC voltage signal may be compensated for by suitable hardware and/or software based methods well known in the art. Linearization improves the accuracy and expands the range of the temperature measured by the TC 101.

Figure 7:
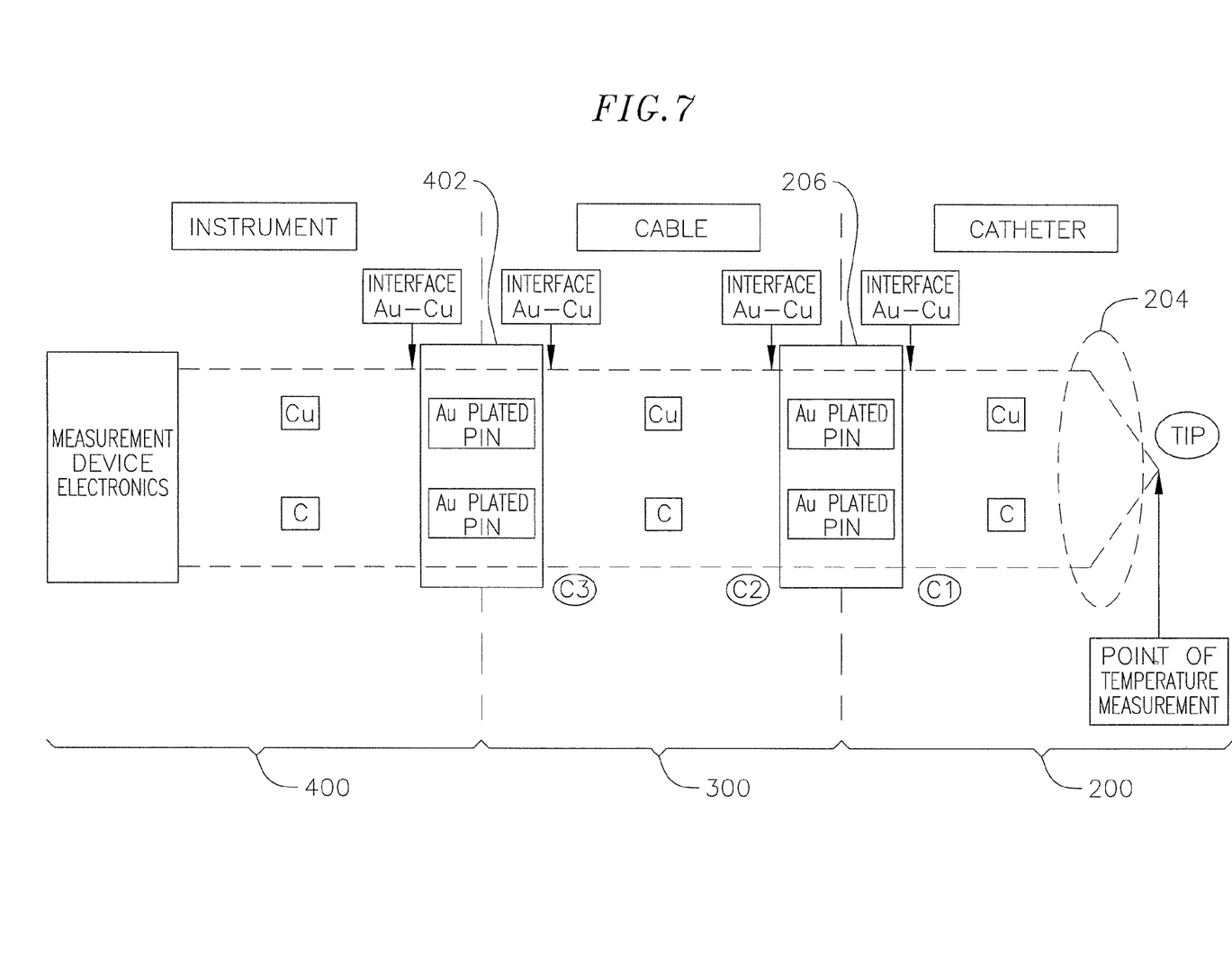
FIG. 7 is a block diagram conceptually illustrating a setup using a conventional catheter for temperature measurement.

FIG. 7 is a block diagram conceptually illustrating a setup using a conventional catheter for temperature measurement.

Referring to FIG. 7, a catheter 200 includes a handle and a T-type TC 204. The hot-junction of the TC 204 may be located at the tip of the catheter 200, and copper and constantan wires of the TC 204 are connected to a cable 300 through handle connectors 206 (e.g., pins and sockets). Here, two TC connections are created due to the handle connectors 206, that is, a connection between the constantan wire of the TC 204 and the gold-plated pin of the handle connector 206 (denoted as C1), and a connection between the constantan wire of the cable 300 and the gold-plated pin of the handle connector 206 (denoted as C2). The other end of the cable 300 is connected to an instrument 400 through front panel connectors 402 (e.g., pins and sockets) of the instrument 400. Here, another two TC connections are created due to the front panel connectors 402, that is, a connection between the constantan wire of the cable 300 and the gold-plated pin of the connector 402 (denoted as C3), and a connection between the constantan wire inside the instrument 400 and the gold-plated pin of the connector 402 (denoted as C4). Since the connectors 206 and 402 are not made of appropriate TC materials to match the constantan wire, each of the TC connections (C1, C2, C3, and C4) introduces an error voltage that causes measurement error.

In the conventional setup of FIG. 7, measuring temperatures using the TC 204 and routing the low level TC voltage signal (e.g., low millivolt range) outputs through multiple connector pairs of dissimilar connector contact pins constructed of different metals/metal-alloys (e.g., non-TC metals) to temperature reading instrumentation (e.g., instrument 400) creates measurement errors since the TC voltage signal is degraded through successive connection points of dissimilar materials.

According to embodiments of the present invention, TC signal degradation may be eliminated or reduced by implementing a TC signal-processing circuit in a catheter handle to digitize the TC voltage signal at the cold-junction at the catheter handle.

Figure 8:
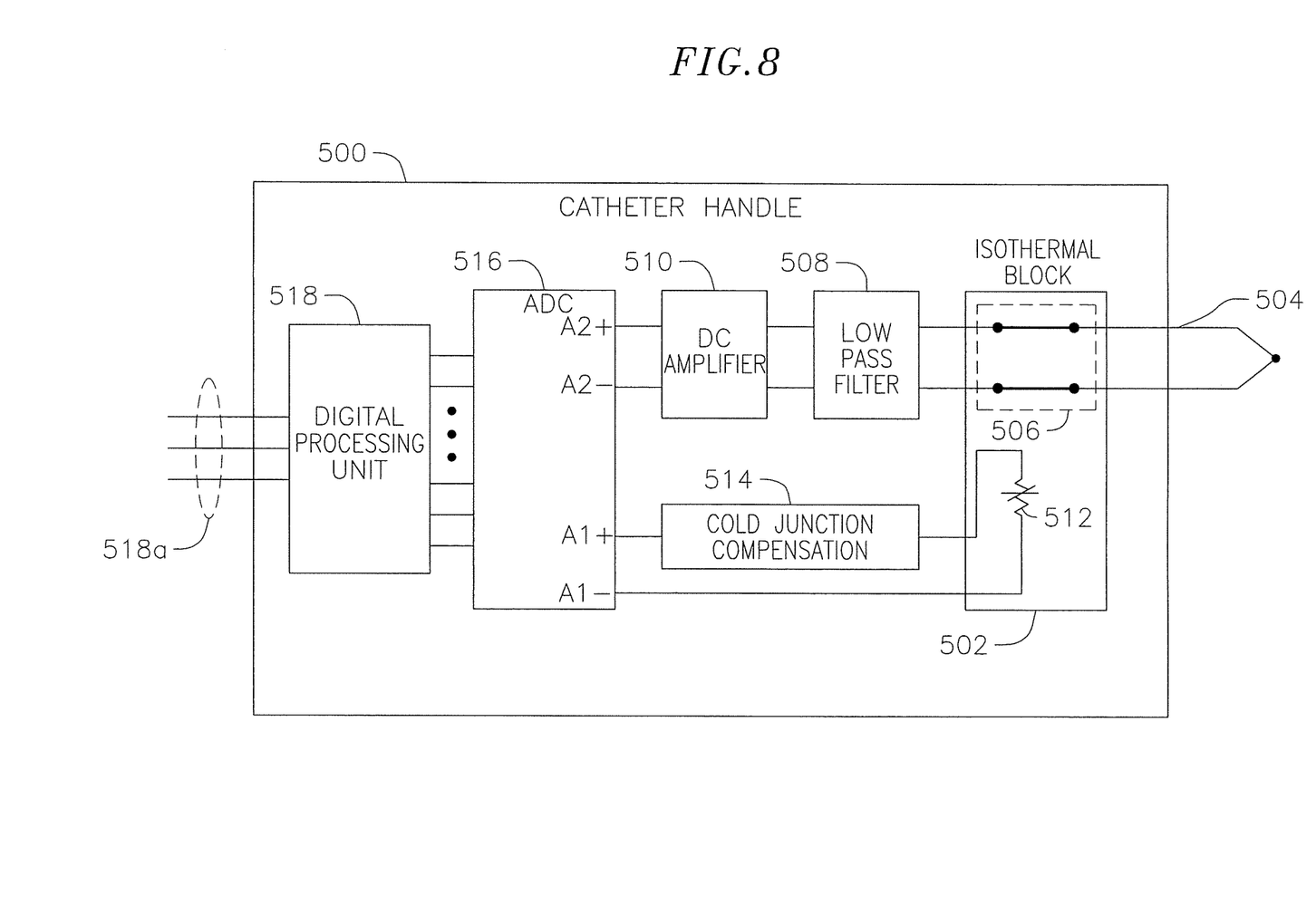
FIG. 8 is a drawing conceptually illustrating a catheter handle including a TC signal-processing circuit according to an embodiment of the present invention.

FIG. 8 is a drawing conceptually illustrating a catheter handle 500 including a TC signal-processing circuit according to an embodiment of the present invention.

Referring to FIG. 8, a TC signal-processing circuit located inside the catheter handle 500 includes a cold-junction isothermal block 502 that receives a TC 504 from a catheter shaft (not shown). The isothermal block 502 may be maintained by a small slab of material with high thermal conductivity such as copper or other suitable materials with high thermal conductivity. The input connections 506, to which the TC 504 is connected to, are electrically isolated but thermally linked through the isothermal block 502. In one embodiment, the whole signal-processing circuit may be included in the isothermal block 502. In addition, the signal-processing circuit may include a low pass filter 508, a low-level DC amplifier 510, a temperature sensor 512, a cold-junction compensation circuit 514, an analog-to-digital (A/D) converter 516, and a digital processing unit 518. In some embodiments, the A/D converter 516 and the digital processing unit 518 may be included in the same circuit module (e.g., an integrated circuit). Furthermore, one skilled in the art will understand that the above described signal-processing circuit may include some or all of the elements as described and may include additional circuit elements well known in the art.

The low pass filter 508 eliminates or reduces signal saturation, for example, due to ablation signal pick-up when the catheter is an ablation catheter. In some embodiments, the low pass filter 508 may be omitted. The A/D converter 516 digitizes the TC voltage signal to its corresponding digital value which is processed by the digital processing unit 518. For example, the digital processing unit 518 may provide functions such as open-thermocouple detection and alarming, cold-junction compensation, linearization, and calculating the temperature sensed by the TC 504. In addition, the digital processing unit 518 includes a digital interface 518a for data communication with a host (e.g., a computer or a controller) through a digital link such that the digitized data of the TC 504 may be transmitted to the host for further processing or display. However, the present invention is not limited to the above described TC signal-processing circuit. To the contrary, the TC signal-processing circuit in the catheter handle 500 may have various modifications and equivalent arrangements. Furthermore, the digital processing unit 518 may not calculate the temperature of the TC 504, but, may transmit the digitized TC voltage through the digital interface 518a to the host which calculates the temperature of the TC 504 based on the value of digitized TC voltage signal.

As described in the embodiment of FIG. 8, digitizing TC voltage signal at the catheter handle 500 reduces the number of material transitions through connectors and the overall system, therefore, measurement errors associated with those transitions may be avoided. The catheter handle 500 may be connected with the host with any suitable digital links such as a 1-Wire communication connection. Accordingly, special TC wirings such as constantan wire may be avoided in the connection wirings between the catheter handle 500 and the host, thus decreasing cost significantly.

Exemplary Embodiments

Hereinafter, exemplary embodiments of the present invention will be disclosed to further illustrate the various aspects and features of the present invention. However, these exemplary embodiments are merely illustrative and the present invention is not limited thereto.

Figure 9:
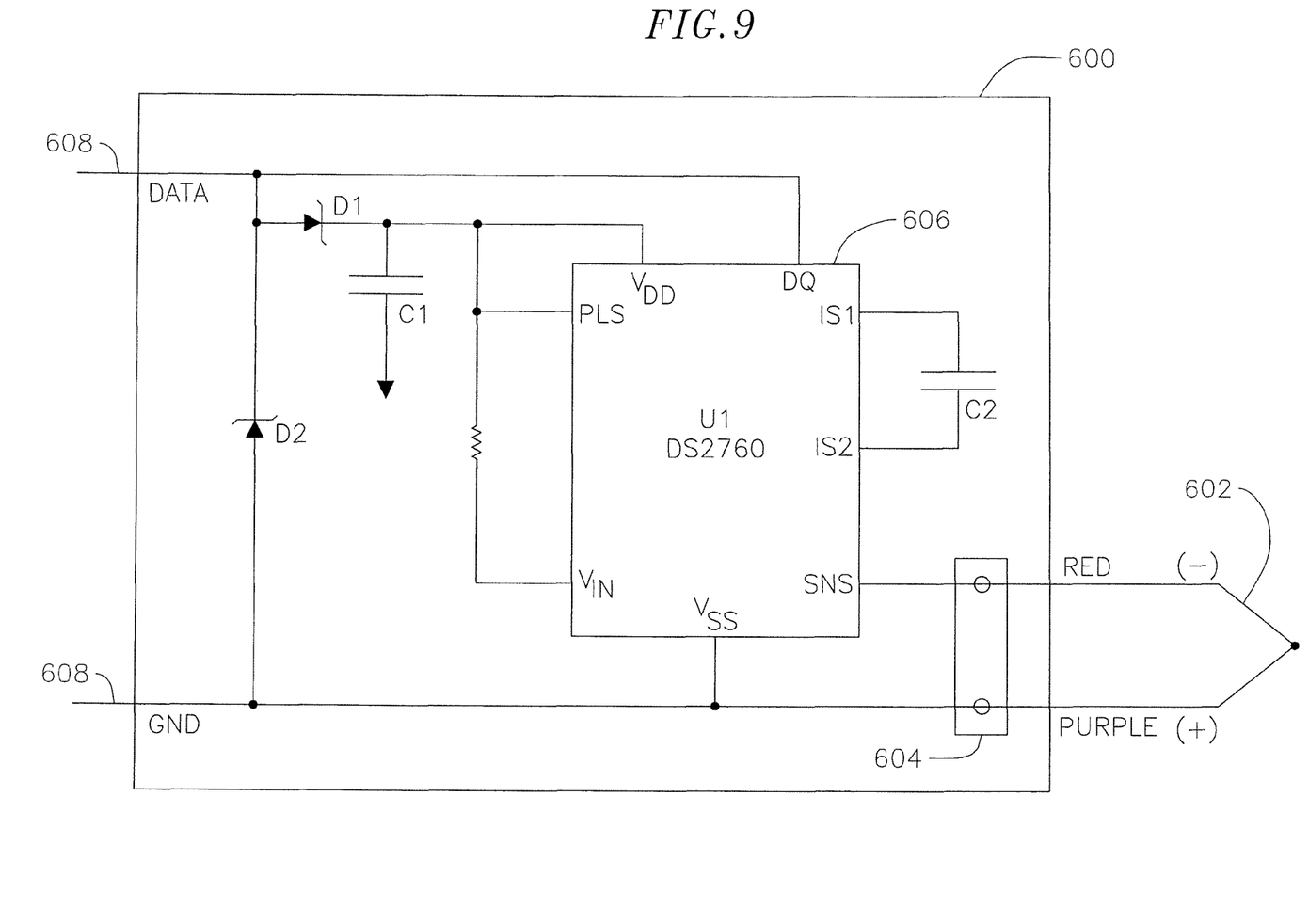
FIG. 9 is a drawing schematically illustrating a TC signal-processing circuit according to an embodiment of the present invention.

FIG. 9 is a drawing schematically illustrating a TC signal-processing circuit 600 according to an embodiment of the present invention.

Referring to FIG. 9, the TC signal-processing circuit 600 may be implemented by one or more circuit boards (e.g., printed circuit boards) at a catheter handle. A TC voltage signal is outputted from a TC 602 that is connected to the TC signal-processing circuit 600. Here, the connection between the TC 602 and the TC signal-processing circuit 600 forms the cold-junction 604. The TC voltage signal at the cold-junction 604 is digitized at the catheter handle by an integrated circuit (IC) 606 (e.g., MAXIM, module No. DS2760) that communicates with a host (e.g., a computer) over a digital link 608 (e.g., a single twisted-pair connection, 1-Wire bus, etc.). The IC 606 may have a unique address (e.g., 64-bit address) that permits positive identification and selection by the host or a bus master. Because of this unique address, multiple units of TC signal-processing circuits 600 may share the same digital link 608, and software can automatically recognize and process data from any given TC connected to one of the signal-processing circuits 600. Information associated with the TC 602 may be stored within the IC 606 itself. Alternatively, the unique address of the IC 606 allows the information associated with the TC 602 and other reference data to be stored at the host or bus master. In one embodiment of the present invention, the IC 606 communicates with a single bus master via a 1-Wire bus (i.e., the digital link 680). Here, the single bus master executes touch memory executive (TMEX) protocol to control the IC 606, and bidirectional data and power are transmitted over the 1-Wire bus. Data transfers may be processed half duplex and bit sequential using short and long time slots to encode the binary ones and zeros respectively, while power is transmitted during communication idle times.

As described in the embodiment of FIG. 9, the IC 606 digitizes the millivolt level voltage produced between the hot and cold junctions of the TC 602, while its on-chip temperature sensor continuously monitors the temperature at the cold-junction 604. The unique address of the IC 606 permits multiple units of signal-processing circuits 600 to operate on the same digital link 608. In addition, the IC 606 may contain user-accessible memory for storage of sensor-specific data such as TC type, location, and the date it was put into service. This allows the IC 606 to be used with any TC type because the host or bus master uses the stored data to determine the correct calculations to make based on the type of TC in use and the temperature of the cold-junction as reported by the on-chip temperature sensor.

In FIG. 9, the IC 606 is a MAXIM DS2760 which provides a complete signal conditioning and digitizing solution for use with TC 602, the DS2760 includes a 10-bit voltage A/D converter, a 13-bit temperature A/D converter, and a 12-bit plus-sign current A/D converter. It also provides 32 bytes of lockable EEPROM memory where pertinent user or sensor documentation may be stored, minimizing the probability of error due to TC mislabeling. Here, the TC 602 may be directly connected to the A/D converter current inputs of the DS2760. With a full-scale range of ±64 mV (LSB of 15.625 µV), the A/D converter of the DS2760 provides resolution better than 1° C., even with the lower voltage output of a type-K TC.

Accordingly, the DS2760 (i.e., IC 606) may be used to convert a standard TC into a smart sensor with multi-drop capability. In FIG. 9, a capacitor C1 and a Schottky diode D1 form a half-wave rectifier that provides power for the DS2760 by taking power from the bus (i.e., digital link 680) during idle communication periods when the bus is at 5 V. A Schottky diode D2 is connected across DATA and GND of the bus to provide circuit protection by restricting signal excursions that go below ground to about −0.4 V. Without the diode D2, negative signal excursions on the bus exceeding 0.6 V may forward bias the parasitic substrate diode of the DS2760 and interfere with its proper functioning. Under bus master control, the DS2760 monitors the voltage developed between the hot and cold junctions of the TC 602 and uses its internal temperature sensor to measure the temperature at the cold junction 604. The bus master uses this information to calculate the actual temperature at the hot-junction. When attaching the TC 602 to the signal-processing circuit 600, it should be connected as close as possible to the DS2760 so that minimal temperature difference exists between these connections and the circuit inside the DS2760 IC package.

To maintain the connections at the cold-junction 604 at substantially the same temperature, proper use of copper trace and lead placement techniques can create an isothermal block in and around the points where the TC leads attach to the copper traces of the signal-processing circuit 600. Because temperature differentials generate voltage differentials, printed circuit board traces should be routed together, and equal numbers of junctions maintained on each conductor effectively replace the expensive TC extension cable used within the conventional catheter handle. The DS2760 digitizes the millivolt-level voltage signal produced between the hot and cold junctions of two dissimilar metals at a given temperature due to the Seebeck effect, and communicates the information to the host or master so that correct temperature at the hot-junction may be calculated. In some embodiments, the signal-processing circuit 600 may communicate with the host by a wireless data link.

Figure 10:
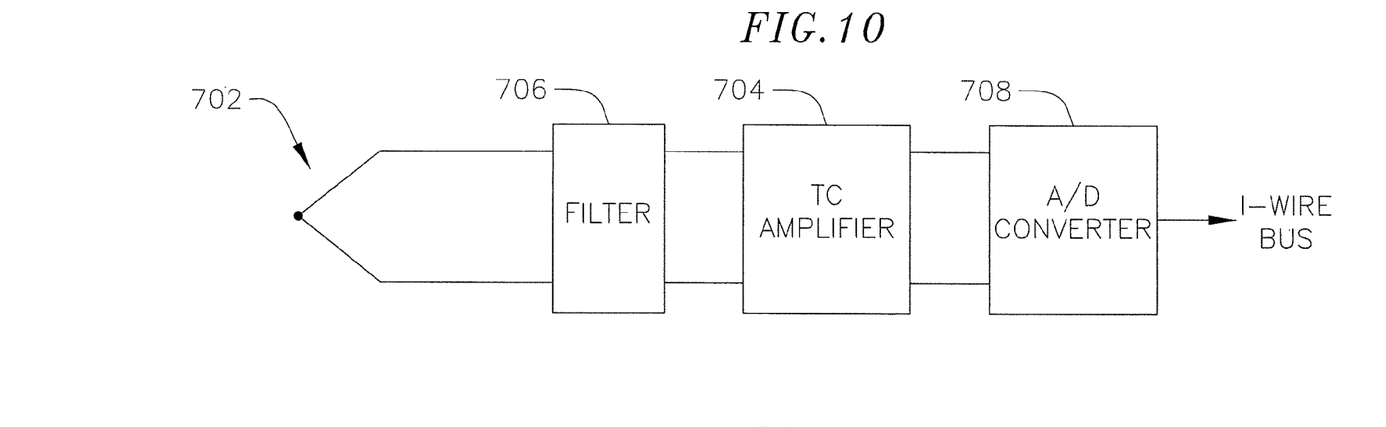
FIGS. 10, 11 and 12 illustrate additional exemplary embodiments of a TC signal-processing circuit according to the present invention.
Figure 11:
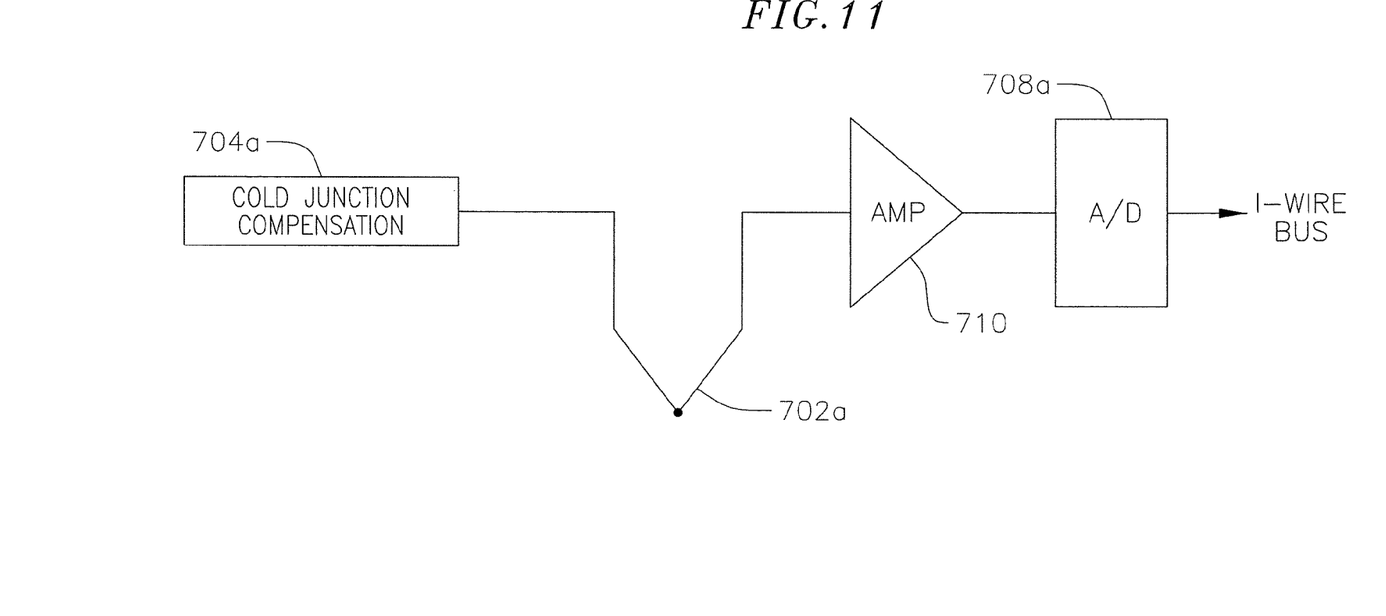
Figure 12:
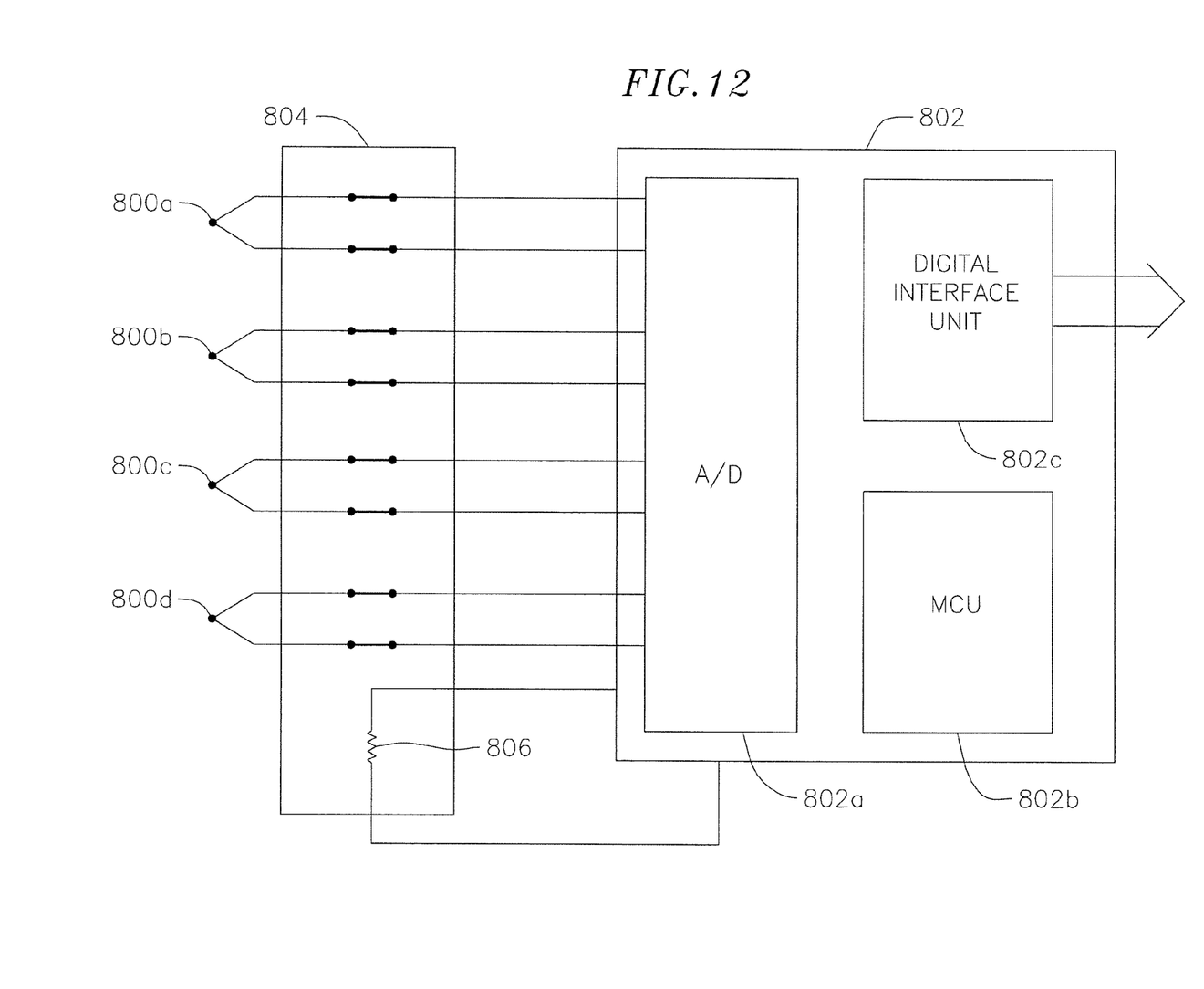

FIGS. 10, 11 and 12 illustrate additional exemplary embodiments of the signal-processing circuit 600 according to the present invention. Since the techniques of their implementation are within the knowledge of one skilled in the art, detailed description thereof will be omitted.

In the embodiment of FIG. 10, the signal-processing circuit 600 includes a TC 702 connected to a suitable TC amplifier 704 with cold-junction compensation (e.g., ANALOG DEVICES Model No. AD594/AD595). A suitable ablation signal reduction unit 706 (e.g., a ferrite unit) may be connected between the TC 702 and the amplifier 704 to filter ablation signal pick-up when the catheter is an ablation catheter. The amplifier 704 sends cold-junction compensated TC voltage signal to a 1-Wire A/D converter chip 708 (e.g., MAXIM Model No. DS2450) to be digitized and transmitted through a 1-Wire bus to a host.

In the embodiment of FIG. 11, the signal-processing circuit 600 includes a TC 702*a* connected to a suitable TC cold-junction compensator 704*a* (e.g., LINEAR TECHNOLOGY Model No. LT1025) and a suitable amplifier 710. The analog output of the amplifier 710 is converted to digital value by a 1-Wire A/D converter chip 708*a* (e.g., MAXIM Model No. DS2450) to be transmitted through a 1-Wire bus to a host.

In FIG. 12, the signal-processing circuit 600 includes a processing module 802 (e.g., BURR-BROWN Model No. MSC1200) connected to a plurality of TCs (800*a*, 800*b*, 800*c*, 800*d*) through an isothermal block 804. The temperature of the isothermal block 804 is measured by the processing module 802 through a temperature sensor 806 to perform cold-junction compensation. The processing module 802 includes an A/D converter 802*a* for converting the analog TC voltage signals into digital values and a microcontroller unit (MCU) 802*b* for calculating the temperatures sensed by the TCs (800*a*, 800*b*, 800*c*, 800*d*) based on the digital values. In addition, the MCU 802b may perform cold-junction compensation and linearization. To transmit the digital data from the signal-processing circuit 600 to a host, the processing module 802 includes a digital interface unit 802c that communicates with the host through a suitable digital link such as SPI, I²C, 1-Wire, etc.

While this disclosure has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A catheter comprising:
    a catheter shaft having a proximal end and a distal end;
    a first pair of conductors extending through the catheter shaft, each one of the first pair of conductors having a first end and a second end, the first ends of the first pair of conductors being coupled to each other at the distal end of the catheter shaft to form a first thermocouple; and
    a handle coupled to the proximal end of the catheter shaft, the second ends of the first pair of conductors being in the handle, the handle comprising a digitizing circuit therein coupled to the second ends of the first pair of conductors for digitizing a voltage signal of the first thermocouple, the handle further comprising an isothermal block thermally coupled to the second ends of the first pair of conductors, and the digitizing circuit is included in the isothermal block.

2. The catheter of claim 1, wherein the digitizing circuit further comprises a temperature sensor for sensing a temperature of the isothermal block.

3. The catheter of claim 1, wherein the digitizing circuit comprises a low pass filter for filtering the voltage signal of the first thermocouple.

4. The catheter of claim 1, wherein the digitizing circuit comprises an amplifier for amplifying the voltage signal of the first thermocouple.

5. The catheter of claim 1, wherein the digitizing circuit comprises an analog-to-digital converter for generating a digital value corresponding to the voltage signal of the first thermocouple.

6. The catheter of claim 5, wherein the digitizing circuit is adapted to calculate a temperature value of the first thermocouple based on the digital value.

7. The catheter of claim 1, wherein the digitizing circuit is adapted to perform cold-junction compensation.

8. The catheter of claim 1, wherein the digitizing circuit is capable of being identified by at least one digital address.

9. The catheter of claim 1, further comprising a second pair of conductors extending through the catheter shaft, each one of the second pair of conductors having a first end and a second end, the first ends of the second pair of conductors being coupled to each other at a portion between the proximal end and the distal end of the catheter shaft to form a second thermocouple,
    wherein the second ends of the second pair of conductors are in the handle, and
    wherein the digitizing circuit is coupled to the second ends of the second pair of conductors, and is adapted to digitize a voltage signal of the second thermocouple.

10. The catheter of claim 9, wherein the digitizing circuit is adapted to calculate a temperature value of the second thermocouple based on the digitized voltage signal of the second thermocouple.

11. The catheter of claim 9, wherein the digitizing circuit is capable of being identified by at least two digital addresses including a first digital address corresponding to the first thermocouple and a second digital address corresponding to the second thermocouple.

12. The catheter of claim 1, wherein the digitizing circuit comprises a digital interface for transmitting data corresponding to the voltage signal of the first thermocouple.

13. A system for measuring temperature comprising:
    a host; and
    a catheter in data communication with the host, the catheter comprising:
        a catheter shaft having a proximal end and a distal end;
        a pair of conductors extending through the catheter shaft, each one of the pair of conductors having a distal end and a proximal end, the distal ends of the pair of conductors being coupled to each other at the distal end of the catheter shaft to form a thermocouple; and
        a handle coupled to the proximal end of the catheter shaft, the proximal ends of the pair of conductors being in the handle, the handle comprising a digitizing circuit coupled to the proximal ends of the pair of conductors for digitizing a voltage signal of the thermocouple, the handle further comprising an isothermal block thermally coupled to the proximal ends of the pair of conductors, wherein the digitizing circuit is included in the isothermal block.

14. The system of claim 13, wherein the digitizing circuit comprises an analog-to-digital converter for generating a digital value corresponding to the voltage signal of the thermocouple.

15. The system of claim 14, wherein the digitizing circuit is adapted to calculate a temperature value of the thermocouple based on the digital value.

16. The system of claim 15, wherein the digitizing circuit comprises a digital interface for transmitting data corresponding to the voltage signal of the thermocouple.

17. A method of measuring temperature with a catheter, the method comprising:
    sensing a temperature at a distal end of a catheter shaft of the catheter by a thermocouple, the catheter comprising a pair of conductors extending through the catheter shaft, each one of the pair of conductors having a first end and a second end, the first ends of the pair of conductors being coupled to each other at the distal end of the catheter shaft to form the thermocouple;
    transmitting a voltage signal of the thermocouple to a handle coupled to a proximal end of the catheter shaft; and
    digitizing the voltage signal of the thermocouple by a circuit located at the handle to generate a digital value corresponding to the temperature, the handle comprising an isothermal block thermally coupled to the second ends of the pair of conductors, wherein the circuit is included in the isothermal block.

18. The method of claim 17, further comprising performing cold-junction compensation by the circuit located at the handle.

19. The method of claim 17, further comprising processing the voltage signal of the thermocouple by a low pass filter.

20. The method of claim 17, further comprising transmitting the digital value to a host located away from the handle by a digital link.

* * * * *